(12) United States Patent
Uemasu et al.

(10) Patent No.: US 7,030,237 B2
(45) Date of Patent: Apr. 18, 2006

(54) METHOD AND EQUIPMENT FOR CONTINUOUS AND SELECTIVE INCLUSION SEPARATION

(75) Inventors: Isamu Uemasu, c/o Aist Tsukuba West, National Institute of Advanced Industrial Science and Technology, 16-1, Onogawa, Tsukuba, Ibaraki 305-8569 (JP); Kozo Hara, Yokohama (JP); Hideki Takahashi, Yokohama (JP)

(73) Assignees: National Institute of Advanced Industrial Science and Technology, Tokyo (JP); Ensuiko Sugar Refining Co. Ltd., Kanagawa (JP); Bio Research Corporation of Yokohama, Kanagawa (JP); Isamu Uemasu, Ibaraki (JP)

( * ) Notice: Subject to any disclaimer, the term of this patent is extended or adjusted under 35 U.S.C. 154(b) by 273 days.

(21) Appl. No.: 10/009,627

(22) PCT Filed: Dec. 21, 2000

(86) PCT No.: PCT/JP00/09073

§ 371 (c)(1),
(2), (4) Date: Oct. 26, 2001

(87) PCT Pub. No.: WO01/64606

PCT Pub. Date: Sep. 7, 2001

(65) Prior Publication Data

US 2003/0073831 A1   Apr. 17, 2003

(30) Foreign Application Priority Data

Mar. 3, 2000 (JP) .............................. 2000-59431

(51) Int. Cl.
*C08B 37/16* (2006.01)

(52) U.S. Cl. .................... 536/103; 536/46; 536/123.1; 536/124; 536/122; 536/127; 149/2; 510/207; 514/338; 585/865

(58) Field of Classification Search ................ 536/103, 536/46, 123.1, 124, 122, 127; 585/865; 149/2; 510/207; 514/338
See application file for complete search history.

(56) References Cited

U.S. PATENT DOCUMENTS 5,095,173 A * 3/1992 Uemasu et al. ............. 585/865

(Continued)

OTHER PUBLICATIONS

Armstrong et al. "Enrichment of Enantiomers and other isomers with aqueous liquid membranes containing cyclodextrin carriers." Anal Chem. 59, 2237-2241, 1987.*

(Continued)

*Primary Examiner*—James O. Wilson
*Assistant Examiner*—Devesh Khare
(74) *Attorney, Agent, or Firm*—Norris McLaughlin & Marcus PA

(57) ABSTRACT

In a reaction system having at least two liquid-liquid interfaces between an organic phase of raw material containing a compound(s) to be separated and an aqueous phase of an aqueous solution of inclusion-complexing agent and between that aqueous phase and an organic phase(s) of extraction solvent(s), the compound(s) to be separated is entrapped into the aqueous phase through formation of an inclusion complex(es) of the inclusion-complexing agent with the compound(s), while the compound(s) is entrapped into the organic phase(s) of extraction solvent(s) through dissociation of said inclusion complex(es). The foregoing operation is performed using, for example, a squarish U-shaped tube or an H-shaped tube with bottom plates. Preferred examples of inclusion-complexing agent include highly water-soluble branched cyclodextrins.

4 Claims, 3 Drawing Sheets

U.S. PATENT DOCUMENTS 5,177,302 A * 1/1993 Uemasu et al. ............. 585/864

OTHER PUBLICATIONS

Katsutoshi Nagai and Hans-Georg Elias; "Polymerization of Micellized 1-O-3-(4-vinylphenyl)propyl-β-D-glucopyranose"; Markromol. Chem. 188, 1095-1127 (1987).

Jian Wang and Isiah M. Warner; "Chiral Separations Using micellar Electrokinetic Capillary Chromatography and a Polymerized Chiral Micelle"; Anal. Chem. 1994, 66, 3773-3776.

Daniel W. Armstrong and Heng L. Jin; "Enrichment of Enantiomers and Other Isomers with Aqueous Liquid Membranes Containing Cyclodextrin Carriers" Anal. Chem. 1987, 59, 2237-2241.

* cited by examiner

METHOD AND EQUIPMENT FOR CONTINUOUS AND SELECTIVE INCLUSION SEPARATION

This application is a 371 of PCT/JP00/09073, filed Dec. 21, 2000, which claims foreign priority benefit under 35 U.S.C. § 119 of the Japanese Patent Application No. 2000-59431 filed Mar. 3, 2000.

TECHNICAL FIELD

The present invention relates to a method of effectively separating a variety of compound(s) as an object(s) of separation useful as a starting material(s) of chemical syntheses and/or the like, and a separator for use therein. Raw materials that can be subjected to the method of the present invention are a wide variety of raw materials, examples of which include disubstituted benzene isomer mixtures such as xylene isomer mixtures, trisubstituted benzene isomer mixtures such as trimethylbenzene isomer mixtures, methylquinoline isomer mixtures, substituted naphthalene isomer mixtures such as methylnaphthalene isomer mixtures and dimethylnaphthalene isomer mixtures, and optical isomer mixtures of pinene, limonene, menthol, mandelic acid esters, etc.

BACKGROUND ART

Separation of compounds as objects of separation from raw materials as mentioned above is difficult or impossible by a customary distillation or crystallization method, so that special separation methods have been invented for and applied to respective raw materials.

The present inventors and the like had already discovered and patented methods according to which compounds as mentioned above can be highly selectively separated using either an aqueous solution of highly water-soluble substituted cyclodextrin such as branched cyclodextrin or an aqueous alkaline solution of unsubstituted cyclodextrin through formation of inclusion complexes and subsequent liquid-liquid extraction. An organic compound(s) as an object(s) of separation entrapped in an aqueous solution of a cyclodextrin is contacted with an organic solvent such as diethyl ether, or heated at a temperature of at least 60° C., whereby the compound(s) can be dissociated from the cyclodextrin and recovered. However, a continuous process of treatments ranging from entrapment of a compound(s) as an object(s) of separation in an aqueous solution of cyclodextrin to recovery thereof cannot easily be established. This is not limited to a case where a cyclodextrin is used as one kind of inclusion-complexing agent.

Accordingly, an object of this invention is to provide a continuous and selective method of entrapping a compound(s) as an object(s) of separation into an aqueous phase made of an aqueous solution of inclusion-complexing agent, and dissociating and recovering the entrapped compound(s) from the inclusion-complexing agent. Incidentally, the term "selective" used herein refers to a selectivity with which there can be attained an improvement in the purity of a compound as an object of separation, which is sufficient enough to provide a possibility of developing an industrially useful process.

DISCLOSURE OF THE INVENTION

The present invention provides a continuous and selective inclusion separation method characterized in that, in a reaction system having at least two liquid-liquid interfaces between an organic phase of raw material containing a compound(s) to be separated and an aqueous phase of an aqueous solution of inclusion-complexing agent and between that aqueous phase and an organic phase(s) of extraction solvent(s), the compound(s) to be separated is entrapped into the aqueous phase through formation of an inclusion complex(es) of the inclusion-complexing agent with the compound(s), while the compound(s) is entrapped into the organic phase(s) of extraction solvent(s) through dissociation of the inclusion complex(es); and an inclusion separator characterized by comprising a reaction vessel constructed so as to allow an aqueous phase of an aqueous solution of inclusion-complexing agent to form liquid-liquid interfaces with at least two organic phases that are an organic phase of raw material containing a compound(s) to be separated and an organic phase(s) of extraction solvent(s), and stirring means for stirring at least neighborhoods of the respective liquid-liquid interfaces. Incidentally, the reaction vessel may be provided with a heating and/or cooling means and/or pipings for feeding and/or withdrawing the aqueous solution of inclusion-complexing agent, the raw material and the extraction solvent(s) if necessary.

According to the present invention, a wide variety of raw material, examples of which include disubstituted benzene isomer mixtures such as xylene isomer mixtures, trisubstituted benzene isomer mixtures such as trimethylbenzene isomer mixtures, methylquinoline isomer mixtures, substituted naphthalene isomer mixtures such as methylnaphthalene isomer mixtures and dimethylnaphthalene isomer mixtures, and optical isomer mixtures of pinene, limonene, menthol, mandelic acid esters, etc., may be contacted with an aqueous phase of an aqueous solution of, e.g., highly water-soluble cyclodextrin such as a branched cyclodextrin as an inclusion-complexing agent to form at least an inclusion complex of the cyclodextrin with a compound contained in the raw material and to be separated, while in parallel the aqueous phase is contacted with a wide variety of extraction solvent such as heptane to dissociate the inclusion complex, whereby the included compound can be recovered in the organic phase of extraction solvent.

In the present invention, one liquid-liquid interface of the aqueous phase of the aqueous solution of inclusion-complexing agent such as a cyclodextrin is an interface with the organic phase of raw material containing a compound(s) to be separated, so that inclusion complexes of inclusion-complexing agent with compounds in the organic phase of raw a material may be yielded toward their formation in accordance with complex formation constants thereof to selectively entrap in the aqueous phase a at compound to be separated. And other liquid-liquid interface(s) of the aqueous phase is an interface(s) with an organic phase(s) of extraction solvent(s), so that the compound(s) entrapped in the aqueous phase and to be separated can be dissociated to be extracted in the organic phase(s) of extraction solvent(s). The foregoing operation can be performed using a reaction vessel, examples of which include a U-shaped tube that may be squarish as shown in FIGS. 1 to 3 and an H-shaped tube with bottom plates (hereinafter referred to simply as an "H-shaped tube" ) as shown in FIGS. 4 to 6 to which the reaction vessel is not limited. Various altered reaction vessels are usable as will be described later.

Figure 1:
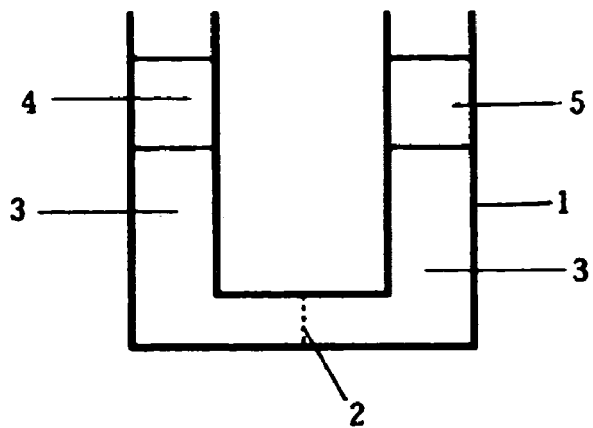
FIG. 1 is a conceptual cross-sectional view illustrating an example of reaction vessel in the basic inclusion separator of the present invention that may be used in the method of the present invention.

EXPLANATION OF SYMBOLS 1, 11, 21 . . . U-shaped tube, 31, 41, 51 . . . H-shaped tube,
2, 22, 32, 42, 52 . . . diaphragm (not an indispensable element),
3, 13, 23, 33, 43, 53 . . . aqueous (cyclodextrin) phase,
4, 14, 24, 34, 44, 54 . . . organic phase of raw material,
5, 15, 25, 35, 45, 55 . . . organic phase of extraction solvent.

MODES FOR CARRYING OUT THE INVENTION

Modes for carrying out this invention will now be described, but should not be construed as limiting the scope of the invention. The following description will be made with priority given to cases where cyclodextrins are used as inclusion-complexing agents. However, it goes without saying that this invention is not limited to these cases in light of the principle of the invention.

When the specific gravity of an organic phase of raw material like a xylene mixture is considerably lower than that of an aqueous phase of an aqueous solution of cyclodextrin (hereinafter often referred to briefly as an "aqueous cyclodextrin phase"), the organic phase of raw material and an organic phase of extraction solvent may be respectively stirred together with the aqueous cyclodextrin phase in a U-shaped tube, whereby inclusion complexation and dissociation-extraction can be effected with improved contact efficiencies. On the other hand, when the specific gravity of the organic phase of raw material is not so lower than or slightly higher than that of the aqueous cyclodextrin phase, the organic phase of raw material is dispersed in or put under the aqueous cyclodextrin phase. When the organic phase of raw material is dissolved into the organic phase of extraction solvent, selective separation is not effected as a matter of course. In this case, the aqueous phase existing between the organic phase of raw material containing a compound(s) to be separated and the organic phase of extraction solvent may be partitioned with a diaphragm permeable to the aqueous solution but hardly permeable to oily droplets to prevent the organic phase of raw material dispersed in the aqueous cyclodextrin phase from migrating into the organic phase of extraction solvent. Examples of the diaphragm include filter paper, filter cloth, nonwoven fabric, net and textile made of fibers of a material, examples of which include cellulose and derivatives thereof, rayon, hairy materials such as wool, silk, plastics, glass, silica, metals, etc.; porous plastic membranes; porous rigid plastic materials formed by sintering a plastic material; ceramic filters formed by sintering ceramic fibers; and sintered stainless filters formed by sintering stainless steel fibers; provided that they may optionally be treated so as to become oil-repellent. Apart from the foregoing case, use of the diaphragm can further improve the contact efficiencies because the organic phase of raw material and the organic phase of extraction solvent can be vigorously stirred together with the aqueous cyclodextrin phase, whereby the rates and efficiencies of inclusion complexation and dissociation-extraction can be enhanced. After withdrawal of the organic phase of extraction solvent and addition of fresh extraction solvent, stirring and extraction may also be continued afresh. Incidentally, where the specific gravity of raw material and/or extraction solvent is higher than that of the aqueous cyclodextrin phase, the H-shaped tube as will be detailed later may advantageously be used. Where the specific gravity of the aqueous cyclodextrin phase is between those of the organic phases of raw material and extraction solvent, an I-shaped tube with a bottom plate may also advantageously be used as the reaction vessel.

At least part of a solution as the organic phase of extraction solvent containing a compound extracted thereinto as an object of separation may advantageously be withdrawn and distilled to concentrate the compound, and the organic solvent separated by distillation may be returned back to the reaction system and reused as the extraction solvent (see Example 27). In this case, the efficiency of extraction can be enhanced because the extraction solvent is refreshed.

The foregoing inclusion complexation and dissociation-extraction operation is performed preferably in the range of 0 to 50° C., more preferably 5 to 40° C., further preferably 10 to 25° C.

Any aqueous phase of cyclodextrin will suffice insofar as it does not yield a solid substance when the cyclodextrin forms any inclusion complexes thereof with any organic compounds to be separated. Needless to say, highly water-soluble substituted cyclodextrins such as branched cyclodextrins can be used in the present invention. Even unmodified cyclodextrins may be used in the operation of the present invention if they are used in the form of an aqueous solution mixed with sodium hydroxide, potassium hydroxide or the like for enhancing the water solubilities thereof and hence enhancing the water solubilities of the resulting inclusion complexes without formation of any solid substance.

Examples of substituted cyclodextrins usable as inclusion-complexing agents in the present invention include substituted cyclodextrins such as α-, β- or γ-cyclodextrin with at least one hydroxyl group thereof having its hydrogen atom substituted with at least one selected from among a glucosyl group, a maltosyl group, maltooligosaccharide residues, a methyl group, a hydroxyethyl group, hydroxypropyl groups, a sulfonic group, alkylenesulfonic groups, and carboxyalkyl groups. Herein, the term "sulfonic group" is intended to encompass not only a group in the free acid form but also groups in a salt form of sodium, potassium, ammonium, lower amine, ethanolamine or the like. The "carboxyl moiety" of "carboxyalkyl group" is intended to have the same meaning as the "sulfonic group." The alkylene moiety of alkylenesulfonic group may be either linear or branched, and is preferably 1 to 5 in the number of carbon atoms. The alkyl moiety of carboxyalkyl group may be either linear or branched, and is preferably 1 to 5 in the number of carbon atoms. Preferred specific examples of usable cyclodextrins include monoglucosyl-α-cyclodextrin, diglucosyl-α-cyclodextrin, triglucosyl-α-cyclodextrin, and mixtures thereof; monomaltosyl-α-cyclodextrin, dimaltosyl-α-cyclodextrin, trimaltosyl-α-cyclodextrin, and mixtures thereof; monoglucosyl-β-cyclodextrin, diglucosyl-β-cyclodextrin, triglucosyl-β-cyclodextrin, and mixtures thereof; monomaltosyl-β-cyclodextrin, dimaltosyl-β-cyclodextrin, trimaltosyl-β-cyclodextrin, and mixtures thereof; 2,6-dimethyl-α-cyclodextrin; and 2,6-dimethyl-β-cyclodextrin.

The suitable cyclodextrin concentration is preferably 5 to 50 wt. %, further preferably 5 to 30 wt. %, based on the aqueous solution.

Examples of raw materials that can be subjected to selective separation with the aid of a cyclodextrin include indole-containing mixtures (Japanese Patent Laid-Open No. 2-200671); disubstituted benzene isomer mixtures such as xylene isomer mixtures, dichlorobenzene isomer mixtures, nitrotoluene isomer mixtures, and chlorobenzotrifluoride isomer mixtures (Japanese Patent Laid-Open Nos. 3-184925 and 6-287149); trisubstituted benzene isomer mixtures such as trimethylbenzene isomer mixtures, trichlorobenzene isomer mixtures, dimethylnitrobenzene isomer mixtures, chloronitrotoluene isomer mixtures, dinitrotoluene isomer mixtures, and xylenol isomer mixtures (Japanese Patent Laid-Open No. 6-87765); 2-methylquinoline-containing hydrocarbon oils (Japanese Patent Laid-Open No. 2-255658); 7-methylquinoline-containing mixtures (Japanese Patent Laid-Open No. 4-321668); 2,6-diisopropylnaphthalene-containing mixtures (Japanese Patent Laid-Open Nos. 2-204419 and 2-209818); 2-methylnaphthalene-containing mixtures (Japanese Patent Laid-Open No. 2-255630); 2,6-dimethylnaphthalene-containing mixtures (Japanese Patent Laid-Open No. 6-116179); and optical isomer mixtures of pinene, limonene, menthol, mandelic acid esters, etc. Incidentally, in the case of raw materials having a determined composition like mixed xylene, the purity of a given compound in the residual organic phase of raw material after subjected to the method of the present invention is improved, so that the residual organic phase of raw material may be repeatedly subjected as raw material to the method of the present invention, whereby that purity can be improved to a desired level.

The amount of the organic phase of raw material containing a compound to be separated is preferably such that the molar ratio of the compound to a cyclodextrin in the aqueous cyclodextrin phase is at least one. Where the raw material is a solid substance, it can be subjected in the form of a solution to separation after it is dissolved in a suitable organic solvent hardly capable of being included in the cyclodextrin.

Organic solvents hardly soluble in water and hardly capable of forming an inclusion complex with a cyclodextrin are preferred as the organic solvent for use in dissociating and extracting a compound entrapped in the aqueous cyclodextrin phase from the cyclodextrin. Examples of such organic solvents include ethers such as diethyl ether, diisopropyl ether, and diisoamyl ether; hydrocarbons such as liquefied propane gas, L P G, liquefied butane gas, pentanes, hexanes, heptanes, and mesitylene; and halogenated hydrocarbons such as dichloromethane. Incidentally, in the case of an extraction solvent highly volatile with a boiling point of at least ordinary temperature and comparatively easily soluble in the aqueous solution of cyclodextrin like diethyl ether, it is preferred to repeat at suitable time intervals the procedure of effecting extraction by stirring for a period of a few seconds to several tens of seconds after addition of the extraction solvent and then recovering the resulting organic solvent layer. In this case, as the extraction solvent in continuing the operation after recovery of the solvent layer, either virgin solvent may be replenished, or the solvent separated from the compound(s) as the object(s) of separation through distillation or the like of the solvent layer may be reused.

When a compound entrapped in the aqueous cyclodextrin phase hardly migrates into the organic phase of extraction solvent or takes time for such migration, a saturating amount of a salt such as sodium chloride, potassium chloride or sodium sulfate may be dissolved in the aqueous cyclodextrin phase to facilitate migration of the included compound into the organic phase of extraction solvent. This is believed to be so because the solubility of the compound entrapped in the aqueous phase is lowered due to a salting-out effect.

Distillation may be used for separating the extracted organic compound from the organic phase of extraction solvent. The organic phase of extraction solvent wherein the compound to be separated is extracted is transferred to a distillation unit, wherein the compound to be separated is concentrated. The extraction solvent separated by distillation may be repeatedly used for extraction. This can reduce the consumption of the extraction solvent.

When a low-boiling solvent boiling below ordinary temperature, e.g., liquefied petroleum gas (LPG), liquefied propane gas or liquefied butane gas, is used as the extraction solvent, a raw material containing a compound(s) to be separated therefrom and an aqueous solution of inclusion-complexing agent are placed in a reaction vessel such as a U-shaped tube or an H-shaped tube in an inclusion separator provided with a pressurizing means, e.g., an apparatus having a reaction vessel placed in an autoclave, and the low-boiling solvent is then placed in the reaction vessel under pressure, followed by stirring to perform a separation operation. After the separation operation, the separator is depressurized to recover the vapor of the low-boiling solvent. During the course of depressurization, heat being generated during liquefaction of the low-boiling solvent vapor through pressurization may be utilized as an (ancillary) means for preventing temperature drop of the organic phase and the aqueous phase in the reaction vessel in keeping with evaporation of the low-boiling solvent (means particularly for preventing the aqueous phase from freezing). The liquefied low-boiling solvent can be reused as the extraction solvent. The extracted organic compound(s) remaining in the reaction vessel is recovered. Alternatively, the organic phase after the extraction operation may be first withdrawn from the reaction vessel into a pressure vessel from which the low-boiling solvent vapor is recovered, instead of direct recovery of the low-boiling solvent vapor from the reaction vessel. In this case as well, heat being generated during pressurization and liquefaction of the low-boiling solvent vapor may of course be used as an (ancillary) means for preventing temperature drop of the residual organic phase(s) and the aqueous phase. Advantages of using a low-boiling solvent boiling below ordinary temperature lie in that a great difference in boiling point between a compound as an object of separation like axylene isomer and an extraction solvent hardly allows the low-boiling solvent to mix in the separated compound, and in that a large-scale and elaborate distillation apparatus may be dispensed with in performing an industrial separation process according to the present invention.

Examples of other inclusion-complexing agents include water-soluble cyclophanes (Kiichi Takemoto, Mikiji Miyata & Keiichi Kimura, "Inclusion Compounds—from Basics to Future Technologies—," Edition 1, published by Tokyo Kagaku Dozin Co., Ltd. on 27th Jun. 1989, pp. 26–27), water-soluble calixarenes (Kiichi Takemoto, Mikiji Miyata & Keiichi Kimura, "Inclusion Compounds—from Basics to Future Technologies—," Edition 1, published by Tokyo Kagaku Dozin Co., Ltd. on 27th Jun. 1989, p. 32), etc. It is further believed that water-soluble polymolecular host compounds difficultly soluble in any organic solvent can be used. It has already been found out that a wide variety of organic compounds including tetrasubstituted benzenes such as durene are included in such inclusion-complexing agents. Water-soluble cyclophanes are cyclized compounds formed, for example, by alternately bonding a plurality of (di) phenylene groups to a plurality of alkylene groups via quaternary ammonium, tertiary sulfonium or monohydroxyammonio-hydroxyethylene groups, provided that the (di)phenylene groups may be modified with hydrophilic groups such as sulfonic groups either in a free acid form or in a salt form. Water-soluble calixarenes are cyclized compounds formed by alternately bonding a plurality of phenolic rings with hydrophilic groups such as sulfonic groups either in a free acid form or in a salt form, at their o-positions, to a plurality of methylene groups (generally constituted of 4 to 8 phenolic rings and 4 to 8 methylene groups), provided that the hydrogen atoms of the phenolic hydroxyl groups may each be substituted with a variety of group.

FIG. 1 is a conceptual cross-sectional view illustrating an example of reaction vessel in the basic inclusion separator of the present invention that may be used in the method of the present invention. The reaction vessel of FIG. 1 is made up of a squarish U-shaped tube 1. FIG. 1 should be considered conceptual because the dimensional ratios and the like in FIG. 1 do not necessarily represent actual values. Although a diaphragm 2 allowing an aqueous solution of inclusion-complexing agent to pass thereacross is drawn in FIG. 1, it is not necessarily an indispensable element. This reaction vessel is first charged with an aqueous phase 3 of an aqueous solution of inclusion-complexing agent, and then charged with an organic phase 4 of raw material and an organic phase 5 of extraction solvent, followed by stirring. Alternatively, there may be adopted a procedure of charging the reaction vessel with the aqueous phase 3 and then the organic phase 4 of raw material, stirring at this stage, subsequently charging it with the organic phase 5 of extraction solvent, and further stirring. Since the amount of the organic phase 4 of raw material decreases with an increasing amount of the organic phase 5 of extraction solvent as stirring is continued, at least part of the organic phase 5 of extraction solvent may be withdrawn with replenishment of the organic phase 4 of raw material if necessary, and fresh extraction solvent may be replenished as needed. Thereafter, the organic phase 5 of extraction solvent is withdrawn as needed, and the organic phase (oil extract) remaining after removal of the extraction solvent is subjected again or repeatedly to the method of the present invention if necessary to heighten the purity of a compound as an object of separation in the oil extract obtained from the organic phase of extraction solvent. Incidentally, the reaction vessels of inclusion separators of FIGS. 2 and 3 used in the following Examples 1 to 9 and 11 to 38 are fundamentally the same as the reaction vessel of FIG. 1.

Figure 4:
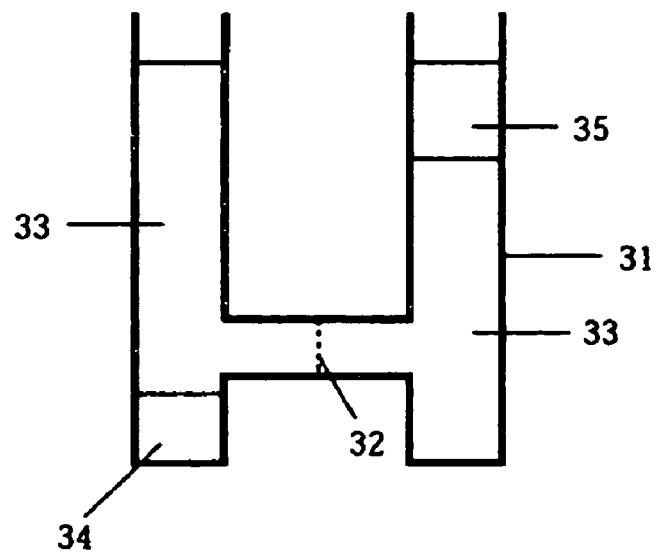
FIG. 4 is a conceptual cross-sectional view illustrating another example of reaction vessel in the basic inclusion separator of the present invention that may be used in the method of the present invention, and showing a state thereof wherein use is made of a raw material higher in specific gravity than an aqueous phase and an extraction solvent lower in specific gravity than the aqueous phase.
Figure 5:
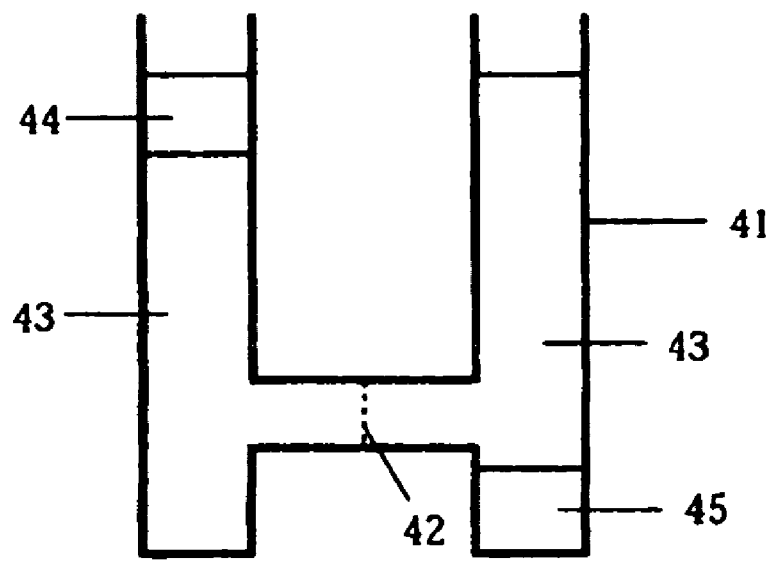
FIG. 5 is a conceptual cross-sectional view illustrating another example of reaction vessel in the basic inclusion separator of the present invention that may be used in the method of the present invention, and showing a state thereof wherein use is made of a raw material lower in specific gravity than an aqueous phase and an extraction solvent higher in specific gravity than the aqueous phase.
Figure 6:
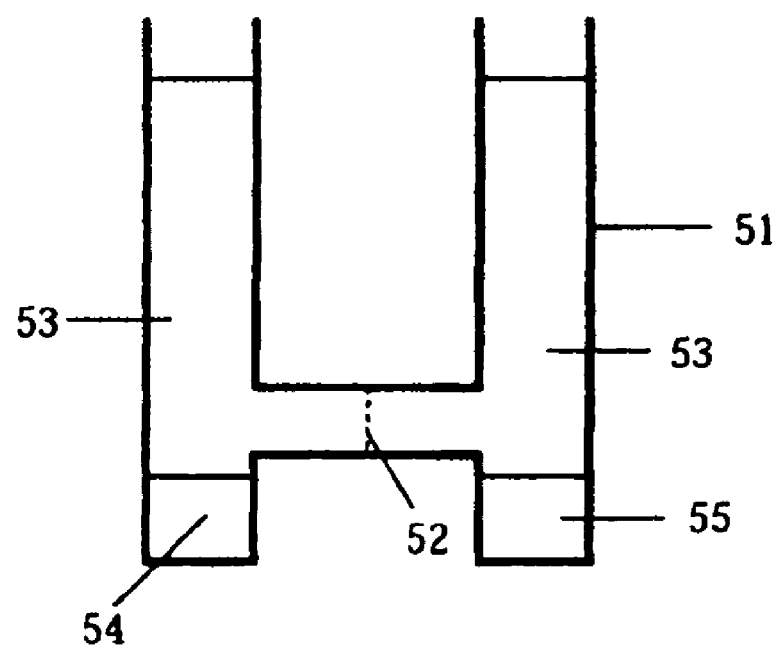
FIG. 6 is a conceptual cross-sectional view illustrating another example of reaction vessel in the basic inclusion separator of the present invention that may be used in the method of the present invention, and showing a state thereof wherein use is made of a raw material and an extraction solvent both higher in specific gravity than an aqueous phase.

FIGS. 4, 5 and 6 are conceptual cross-sectional views illustrating another example of reaction vessel in the basic inclusion separator of the present invention that may be used in the method of the present invention. FIG. 4 shows a state of using a raw material higher in specific gravity than an aqueous phase and an extraction solvent lower in specific gravity than the aqueous phase. FIG. 5 shows a state of using a raw material lower in specific gravity than an aqueous phase and an extraction solvent higher in specific gravity than the aqueous phase. FIG. 6 shows a state of using a raw material and an extraction solvent both higher in specific gravity than an aqueous phase. FIGS. 4, 5 and 6 should be considered conceptual because the dimensional ratios and the like in FIGS. 4, 5 and 6 do not represent the actual values. Although diaphragms 32, 42 and 52 allowing an aqueous solution of inclusion-complexing agent to pass thereacross are drawn in FIGS. 4, 5 and 6, they are not necessarily indispensable elements. In FIGS. 4, 5 and 6, numerals 31, 41 and 51 refer to an H-shaped tube (reaction vessel), 33, 43 and 53 to aqueous phases of aqueous solutions of inclusion-complexing agents, 34, 44 and 54 to organic phases of raw materials, and 35, 45 and 55 to organic phases of extraction solvents. Specifically, a reaction vessel made up of an H-shaped tube is desirably used when the specific gravity of raw material and/or extraction solvent is higher than that of the aqueous solution of inclusion-complexing agent, and is operated in substantially the same manner as in the case where the reaction vessel of FIG. 1 is used. Incidentally, the reaction vessel of inclusion separator used in the following Example 10 is fundamentally the same as the reaction vessel of FIG. 5.

The number of branch tubes extended vertically in a reaction vessel is not limited to 2 but may be 3 or more, and is preferably 2 to 8, more preferably 2 to 6, although it is varied depending on the kind of raw material and the like. A reaction vessel may have at least three branch tubes, so that an aqueous phase of an aqueous solution of inclusion-complexing agent can have at least three liquid-liquid interfaces, one of which is an interface with an organic phase of raw material, and the other two or more of which are respective interfaces with at least two kinds of extraction solvents. In this case, if any difference(s) in extraction selectivity exists between extraction solvents that dissociate and extract compounds to be separated from the respective inclusion complexes [see, e.g., "oil extract" columns in Tables showing results of Example 3 (n-heptane), Example 5 (n-hexane), Example 6 (mesitylene), Example 8 (diisopropyl ether), Example 9 (diisoamyl ether) and Example 10 (dichloromethane)], the purities of separated compounds extracted into the respective extraction solvents can be improved by making the most of any such difference(s) in extraction selectivity to decrease the number of repetitions of the method of the present invention for securing desired purities of respective compounds.

Incidentally, when use is made of an extraction solvent lower in specific gravity than an aqueous solution of inclusion-complexing agent and an extraction solvent higher in specific gravity than the aqueous solution of inclusion-complexing agent, an H-shaped tube may be used Even if a plurality of compounds as the components of raw material are not so different in complex formation constant, the purpose of the present invention may possibly be attained if a plurality of extraction solvents are different in extraction selectivity. In a reaction vessel having, e.g., at least four branch tubes, raw material may be put, for example, into two branch tubes with respectively putting at least two kinds of extraction solvents into the other two or more branch tubes to perform the method of the present invention. Thus, a variety of embodiments are conceivable.

Each vertical tube of a variety of branched tube such as a U-shaped tube or an H-shaped tube may be not only circular but also either elliptic or polygonal such as tetragonal in cross section. The reaction vessel of the inclusion separator is not limited to branched tubes, and may be, for example, in the form of a box-like vessel or a cylinder with a bottom plate (which may be provided with a ceiling plate) provided with a vertical partition having an aperture at a suitable location thereof to form a plurality of compartments, provided that the aperture may be provided with a diaphragm if necessary. An aqueous solution of inclusion-complexing agent is allowed to pass between the compartments via the aperture or the diaphragm.

Although magnetic stirrers were used in Examples, what is essential to stirring for performing the method of the present invention may be sufficient stirring at least neighborhoods of liquid-liquid interfaces. Examples of stirring means include stirring with ultrasonic vibration, stirring with shaking (in forward and backward, leftward and rightward, upward and downward, and/or clockwise and counterclockwise directions), stirring with a stirring rod having agitating blades, etc. Where diaphragms permitting flow thereacross of an aqueous solution of inclusion-complexing agent are attached to a reaction vessel having branch tubes, there may be provided two flow paths making two branch tubes communicate with each other, and the two flow paths may be provided with respective diaphragms and water jet pumps (preferably on the downstream sides of the diaphragms). When two water jet pumps in the flow paths making two branch tubes communicate with each other are actuated to form water streams in mutually opposite directions while sufficiently stirring at least neighborhoods of liquid-liquid interfaces in the branch tubes, the flow of an aqueous solution of inclusion-complexing agent parted by two diaphragms can be promoted while preventing raw material from mixing with extraction solvent due to the diaphragms to perform the extraction operation more efficiently. Of course, such a technical idea can also apply to a case where the reaction vessel is provided with a plurality of compartments. For example, two apertures with short pipes as flow paths may be provided between two compartments, and may be provided with diaphragms and water jet pumps in the same manner as described above. Alternatively, two water propeller fans, which can send water in opposite directions through apertures formed between two compartments and provided with respective diaphragms, may be provided in the respective compartments to perform the extraction operation more efficiently.

EXAMPLES

The following Examples will more specifically illustrate the present invention, but should not be construed as limiting the scope of the invention. The compositions of raw material and oil extract were analyzed according to capillary gas chromatography. Figures in the following Tables indicate the peak area percentages assigned to respective components based on the total of all peak areas for isomers in raw material and oil extract in each gas chromatogram. The following Tables show changes in the composition of components by inclusion complexation and dissociation-extraction. Incidentally, inclusion complexation and dissociation-extraction were effected at room temperature in all the following Examples.

Figure 2:
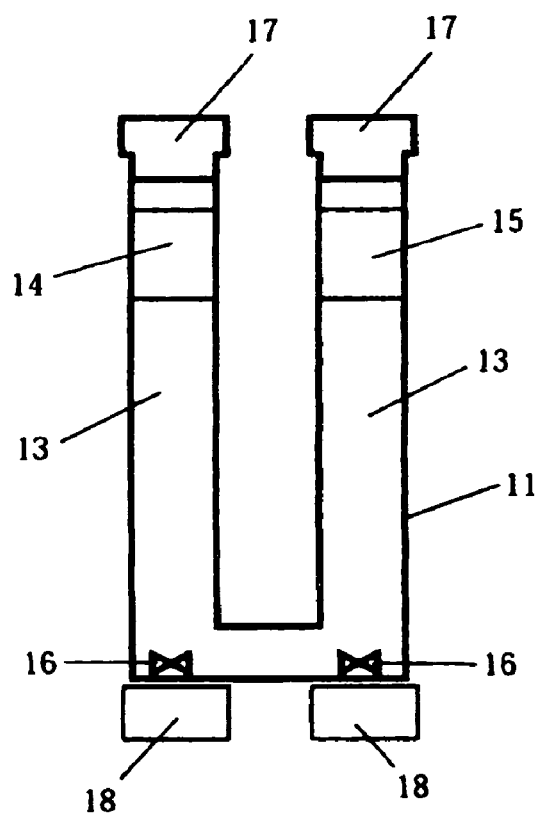
FIG. 2 is a conceptual schematic cross-sectional view of an inclusion separator used in Examples 12 and 28.

FIG. 2 is a conceptual schematic cross-sectional view of an inclusion separator used in Examples 12 and 28, wherein the dimensional ratios and the like of elements do not represent actual ones. The inside diameter of two tubes in vertical direction (vertical tubes) of a reaction vessel in the form of a squarish U-shaped tube 11 is 28 mm, while the inside diameter of a horizontal tube, which is connected with the vertical tubes having respective bottom plates, is 18 mm. The shortest distance between the two vertical tubes is 28 mm, and the height of the vertical tubes is 230 mm. Two magnetic stirrers 18 are installed under the bottom of the reaction vessel of the U-shaped tube 11, while two spinbars 16 are placed in the U-shaped tube 11 The U-shaped tube 11 is sealed by putting plugs 17 therein after fed with an aqueous cyclodextrin phase 13, an organic phase 14 of raw material and an organic phase 15 of extraction solvent. Thereafter, the magnetic stirrers 18 are worked to rotate the spinbars 16, thereby to effect stirring.

Figure 3:
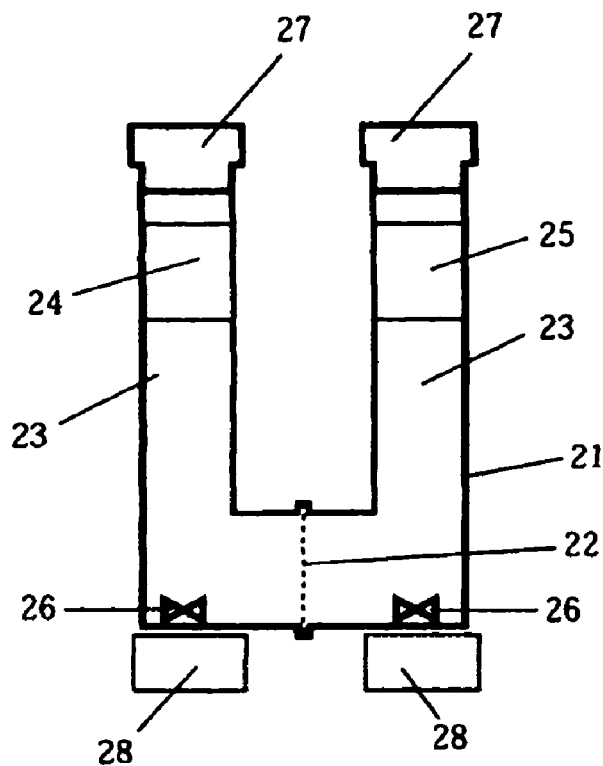
FIG. 3 is a conceptual schematic cross-sectional view of an inclusion separator used in Examples 1 to 9, 11, 13 to 27, and 29 to 38.

FIG. 3 is a conceptual schematic cross-sectional view of an inclusion separator used in Examples 1 to 9, 11, 13 to 27 and 29 to 38, wherein the dimensional ratios and the like of elements do not represent actual ones. The inside diameter of two tubes in vertical direction (vertical tubes) of a reaction vessel in the form of a squarish U-shaped tube 21 is 23 mm, while the inside diameter of a horizontal tube is 30 mm. The horizontal tube having side plates on both ends is connected with the vertical tubes, provided that portions thereof where spinbars 26 are placed are flat. The shortest distance between the two vertical tubes is 60 mm, and the length ranging from the bottom of the reaction vessel of the U-shaped tube 21 to the tops of the two vertical tubes is 100 mm. In FIG. 3, a diaphragm 22 made of filter paper or other material is drawn, but is not used in some Examples. Two magnetic stirrers 28 are installed under the bottom of the reaction vessel of the U-shaped tube 21, while the two spinbars 26 are placed in the U-shaped tube 21. The U-shaped tube 21 is sealed by putting plugs 27 therein after fed with an aqueous cyclodextrin phase 23, an organic phase 24 of raw material and an organic phase 25 of extraction solvent. Thereafter, the magnetic stirrers 28 are worked to rotate the spinbars 26, thereby to effect stirring. In Example 7, however, an aqueous cyclodextrin phase 23 and an organic phase 24 of raw material were placed in the U-shaped tube 21, in which plugs 27 were then put, followed by stirring, while an extraction solvent 26 was subsequently placed in the U-shaped tube 21 after the right plug was pulled out therefrom, followed by reattaching the right plug and then stirring. Incidentally, the "squarish U-shaped tube" of FIG. 2 or 3 will hereinafter referred to simply as the "U-shaped tube." In Example 10 wherein dichloromethane higher in specific gravity than an aqueous cyclodextrin phase was used as extraction solvent, use was made of an H-shaped tube, which was substantially the same as the U-shaped tube of FIG. 3 except for two vertical tubes alone elongated further downward (the length of tubes ranging from the bottoms of the downward-elongated tube portions to the tops of the upward-elongated tube portions is 130 mm). Incidentally, it is a matter of course that an industrial inclusion separator may be provided with a ceiling plate instead of plugs, provided that feed and withdrawal of a raw material, an aqueous solution of inclusion-complexing agent and an extraction solvent are done via pipings.

Example 1

250 ml of a 10 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 15 ml of n-heptane was placed in the other vertical tube. Stirring was effected in such a manner that the xylene phase did not mix with the heptane phase. The composition of xylene isomers extracted in the n-heptane phase after 2 hours is shown in Table 1.

TABLE 1

|  | Raw Material | Oil Extract |
|---|---|---|
| p-Xylene | 49.8% | 76.3% |
| m-Xylene | 50.2% | 23.7% |

Example 2

250 ml of a 10 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 15 ml of n-heptane was placed in the other vertical tube. Vigorous stirring was effected, provided that the bottom portion of the U-shaped tube was partitioned with filter paper. The composition of xylene isomers extracted in the n-heptane phase after 1 hour is shown in Table 2.

TABLE 2

|  | Raw Material | Oil Extract |
|---|---|---|
| p-Xylene | 49.8% | 82.9% |
| m-Xylene | 50.2% | 17.1% |

Example 3

250 ml of a 10 wt. % aqueous solution of a glucosyl-α-cyclodextrin mixture was placed in a U-shaped tube. 6 ml of mixed xylene (commercially available product) was placed in one vertical tube of the U-shaped tube while 6 ml of n-heptane was placed in the other vertical tube. Vigorous stirring was effected, provided that the bottom portion of the U-shaped tube was partitioned with filter paper. The composition of xylene isomers extracted in the n-heptane phase after 2 hours is shown in Table 3.

TABLE 3

|  | Raw Material | Oil Extract |
|---|---|---|
| Ethylbenzene | 15.4% | 20.7% |
| p-Xylene | 18.7% | 49.6% |
| m-Xylene | 44.2% | 24.0% |
| o-Xylene | 21.7% | 5.7% |

Example 4

A solution containing 70 g of sodium chloride dissolved in 250 ml of a 10 wt. % aqueous solution of a glucosyl-α-cyclodextrin mixture was placed in a U-shaped tube. 6 ml of mixed xylene (commercially available product) was placed in one vertical tube of the U-shaped tube while 6 ml of n-hexane was placed in the other vertical tube. Vigorous stirring was effected, provided that the bottom portion of the U-shaped tube was partitioned with filter paper. The composition of xylene isomers extracted in the n-hexane phase after 2 hours is shown in Table 4.

TABLE 4

|  | Raw Material | Oil Extract |
|---|---|---|
| Ethylbenzene | 15.4% | 22.0% |
| p-Xylene | 18.7% | 54.7% |
| m-Xylene | 44.2% | 20.1% |
| o-Xylene | 21.7% | 3.2% |

Example 5

250 ml of a 10 wt. % aqueous solution of a glucosyl-α-cyclodextrin mixture was placed in a U-shaped tube. 6 ml of mixed xylene (commercially available product) was placed in one vertical tube of the U-shaped tube while 6 ml of n-hexane was placed in the other vertical tube. Stirring was effected in such a manner that the xylene phase did not mix with the hexane phase. The composition of xylene isomers extracted in the n-hexane phase after 2 hours is shown in Table 5.

TABLE 5

|  | Raw Material | Oil Extract |
|---|---|---|
| Ethylbenzene | 15.4% | 19.9% |
| p-Xylene | 18.7% | 43.9% |
| m-Xylene | 44.2% | 26.8% |
| o-Xylene | 21.7% | 9.4% |

Example 6

250 ml of a 10 wt. % aqueous solution of a glucosyl-α-cyclodextrin mixture was placed in a U-shaped tube. 6 ml of mixed xylene (commercially available product) was placed in one vertical tube of the U-shaped tube while 6 ml of mesitylene was placed in the other vertical tube. Stirring was effected in such a manner that the xylene phase did not mix with the mesitylene phase. The composition of xylene isomers extracted in the mesitylene phase after 2 hours is shown in Table 6.

TABLE 6

|  | Raw Material | Oil Extract |
|---|---|---|
| Ethylbenzene | 15.4% | 19.2% |
| p-Xylene | 18.7% | 42.4% |
| m-Xylene | 44.2% | 28.7% |
| o-Xylene | 21.7% | 9.7% |

Example 7

250 ml of a 10 wt. % aqueous solution of a glucosyl-α-cyclodextrin mixture was placed in a U-shaped tube. 10 ml of mixed xylene (commercially available product) was placed in one vertical tube of the U-shaped tube. Vigorous stirring was effected, provided that the bottom portion of the U-shaped tube was partitioned with filter paper. After 20 minutes, 5 ml of diethyl ether was added to the other vertical tube of the U-shaped tube, and both spinbars were revolved to effect 5 seconds of vigorous stirring. Thereafter, the liquids were allowed to stand (about 30–60 seconds) until the aqueous cyclodextrin phase was separated from the ether phase. The ether phase was recovered. The composition of xylene isomers extracted in the ether phase is shown in Table 7. Incidentally, initial 20 minutes of stirring was an operation of entrapment into the aqueous phase from mixed xylene through complex formation, while subsequent 5 seconds of stirring was an operation of extracting substances migrated to the aqueous phase into the ether phase through complex dissociation. The short stirring time of 5 seconds was due to a difficulty in phase separation between the aqueous phase and the ether phase if stirred for a long time, because diethyl ether is a little soluble in water.

TABLE 7

|  | Raw Material | Oil Extract |
| --- | --- | --- |
| Ethylbenzene | 15.4% | 20.8% |
| p-Xylene | 18.7% | 50.2% |
| m-Xylene | 44.2% | 24.6% |
| o-Xylene | 21.7% | 4.5% |

Example 8

250 ml of a 10 wt. % aqueous solution of a glucosyl-α-cyclodextrin mixture was placed in a U-shaped tube. 10 ml of mixed xylene (commercially available product) was placed in one vertical tube of the U-shaped tube while 10 ml of diisopropyl ether was placed in the other vertical tube. Vigorous stirring was effected with both spinbars, provided that the bottom portion of the U-shaped tube was partitioned with filter paper. The composition of xylene isomers extracted in the diisopropyl ether phase after 30 minutes is shown in Table 8.

TABLE 8

|  | Raw Material | Oil Extract |
| --- | --- | --- |
| Ethylbenzene | 15.4% | 20.0% |
| p-Xylene | 18.7% | 46.7% |
| m-Xylene | 44.2% | 24.4% |
| o-Xylene | 21.7% | 8.9% |

Example 9

260 ml of a 10 wt. % aqueous solution of a glucosyl-α-cyclodextrin mixture was placed in a U-shaped tube. 10 ml of mixed xylene (commercially available product) was placed in one vertical tube of the U-shaped tube while 10 ml of diisoamyl ether was placed in the other vertical tube. Vigorous stirring was effected, provided that the bottom portion of the U-shaped tube was partitioned with filter paper. The composition of xylene isomers extracted in the diisoamyl ether phase after 30 minutes is shown in Table 9.

TABLE 9

|  | Raw Material | Oil Extract |
| --- | --- | --- |
| Ethylbenzene | 15.4% | 20.4% |
| p-Xylene | 18.7% | 41.5% |
| m-Xylene | 44.2% | 26.3% |
| o-Xylene | 21.7% | 11.8% |

Example 10

250 ml of a 10 wt. % aqueous solution of a glucosyl-α-cyclodextrin mixture was placed in an H-shaped tube. 10 ml of mixed xylene (commercially available product) was placed in one vertical tube of the H-shaped tube while 5 ml of dichloromethane was placed in the other vertical tube. Vigorous stirring was effected, provided that the horizontal pipe portion of the H-shaped tube was partitioned with filter paper. The composition of xylene isomers extracted in the dichloromethane phase after 1 hour is shown in Table 10.

TABLE 10

|  | Raw Material | Oil Extract |
| --- | --- | --- |
| Ethylbenzene | 15.4% | 21.0% |
| p-Xylene | 18.7% | 52.3% |
| m-Xylene | 44.2% | 22.2% |
| o-Xylene | 21.7% | 4.5% |

Example 11

250 ml of a 10 wt. % aqueous solution of a maltosyl-β-cyclodextrin mixture was placed in a U-shaped tube. 20 ml of mixed xylene (commercially available product) was placed in one vertical tube of the U-shaped tube while 20 ml of n-heptane was placed in the other vertical tube. Stirring was effected in such a manner that the xylene phase did not mix with the heptane phase. The composition of xylene isomers extracted in the n-heptane phase after 1 hour is shown in Table 11.

TABLE 11

|  | Raw Material | Oil Extract |
| --- | --- | --- |
| Ethylbenzene | 15.5% | 13.0% |
| p-Xylene | 18.6% | 17.8% |
| m-Xylene | 43.2% | 30.9% |
| o-Xylene | 22.7% | 38.2% |

Example 12

100 ml of a 10 wt. % aqueous solution of 2,6-dimethyl-α-cyclodextrin was placed in a U-shaped tube. 5 ml of mixed xylene (commercially available product) was placed in one vertical tube of the U-shaped tube while 5 ml of n-heptane was placed in the other vertical tube. Stirring was effected in such a manner that the xylene phase did not mix with the heptane phase. The composition of xylene isomers extracted in the n-heptane phase after 1 hour is shown in Table 12.

TABLE 12

|  | Raw Material | Oil Extract |
| --- | --- | --- |
| Ethylbenzene | 15.4% | 26.0% |
| p-Xylene | 18.7% | 17.5% |
| m-Xylene | 44.2% | 42.7% |
| o-Xylene | 21.7% | 13.8% |

Example 13

250 ml of a 10 wt. % aqueous solution of a glucosyl-α-cyclodextrin mixture was placed in a U-shaped tube. 6 ml of a mixture of o-nitrotoluene, m-nitrotoluene and p-nitrotoluene was placed in one vertical tube of the U-shaped tube while 6 ml of n-heptane was placed in the other vertical tube. Vigorous stirring was effected, provided that the bottom portion of the U-shaped tube was partitioned with filter paper. The composition of nitrotoluene isomers extracted in the n-heptane phase after 2 hours is shown in Table 13.

TABLE 13

|  | Raw Material | Oil Extract |
| --- | --- | --- |
| o-Nitrotoluene | 34.6% | 13.6% |
| m-Nitrotoluene | 33.0% | 27.7% |
| p-Nitrotoluene | 32.4% | 58.7% |

Example 14

250 ml of a 10 wt. % aqueous solution of a glucosyl-α-cyclodextrin mixture was placed in a U-shaped tube. 1 ml of a mixture of o-chlorotoluene, m-chlorotoluene and p-chlorotoluene was placed in one vertical tube of the U-shaped tube while 10 ml of n-heptane was placed in the other vertical tube. Vigorous stirring was effected, provided that the bottom portion of the U-shaped tube was partitioned with filter paper. The composition of chlorotoluene isomers extracted in the n-heptane phase after 2 hours is shown in Table 14.

TABLE 14

|  | Raw Material | Oil Extract |
| --- | --- | --- |
| o-Chlorotoluene | 33.5% | 17.1% |
| m-Chlorotoluene | 33.0% | 29.5% |
| p-Chlorotoluene | 33.5% | 53.3% |

Example 15

250 ml of a 10 wt. % aqueous solution of a glucosyl-α-cyclodextrin mixture was placed in a U-shaped tube. 0.5 ml of a mixture of o-chlorobenzotrifluoride, m-chlorobenzotrifluoride and p-chlorobenzotrifluoride was placed in one vertical tube of the U-shaped tube while 5 ml of n-heptane was placed in the other vertical tube. Vigorous stirring was effected, provided that the bottom portion of the U-shaped tube was partitioned with filter paper. The composition of chlorobenzotrifluoride isomers extracted in the n-heptane phase after 2 hours is shown in Table 15.

TABLE 15

|  | Raw Material | Oil Extract |
| --- | --- | --- |
| o-Chlorobenzotrifluoride | 33.2% | 31.8% |
| m-Chlorobenzotrifluoride | 29.6% | 14.1% |
| p-Chlorobenzotrifluoride | 37.1% | 54.1% |

Example 16

250 ml of a 10 wt. % aqueous solution of a glucosyl-α-cyclodextrin mixture was placed in a U-shaped tube. 1.8 ml of a mixture of 3 trimethylbenzene isomers, i.e., mesitylene, pseudocumene and hemimellitene, was placed in one vertical tube of the U-shaped tube while 5 ml of n-heptane was placed in the other vertical tube. Vigorous stirring was effected, provided that the bottom portion of the U-shaped tube was partitioned with filter paper. The composition of trimethylbenzene isomers extracted in the n-heptane phase after 3 hours is shown in Table 16.

TABLE 16

|  | Raw Material | Oil Extract |
| --- | --- | --- |
| Mesitylene | 33.0% | 16.2% |
| Pseudocumene | 34.0% | 17.9% |
| Hemimellitene | 33.0% | 65.9% |

Example 17

250 ml of a 10 wt. % aqueous solution of a maltosyl-β-cyclodextrin mixture was placed in a U-shaped tube. 1.8 ml of a mixture of 3 trimethylbenzene isomers, i.e., mesitylene, pseudocumene and hemimellitene, was placed in one vertical tube of the U-shaped tube while 5 ml of n-heptane was placed in the other vertical tube. Vigorous stirring was effected, provided that the bottom portion of the U-shaped tube was partitioned with filter paper. The composition of trimethylbenzene isomers extracted in the n-heptane phase after 3 hours is shown in Table 17.

TABLE 17

|  | Raw Material | Oil Extract |
| --- | --- | --- |
| Mesitylene | 33.0% | 18.4% |
| Pseudocumene | 34.0% | 59.5% |
| Hemimellitene | 33.0% | 22.1% |

Example 18

250 ml of a 10 wt. % aqueous solution of a glucosyl-α-cyclodextrin mixture was placed in a U-shaped tube. 6 ml of a mixture of 3 trichlorobenzene isomers, i.e., 1,3,5-trichlorobenzene, 1,2,4-trichlorobenzene and 1,2,3-trichlorobenzene, was placed in one vertical tube of the U-shaped tube while 6 ml of n-heptane was placed in the other vertical tube. Vigorous stirring was effected, provided that the bottom portion of the U-shaped tube was partitioned with filter paper. The composition of trichlorobenzene isomers extracted in the n-heptane phase after 1 hour is shown in Table 18.

TABLE 18

|  | Raw Material | Oil Extract |
| --- | --- | --- |
| 1,3,5-Trichlorobenzene | 34.3% | 23.8% |
| 1,2,4-Trichlorobenzene | 33.0% | 21.3% |
| 1,2,3-Trichlorobenzene | 32.7% | 54.9% |

Example 19

250 ml of a 10 wt. % aqueous solution of a glucosyl-α-cyclodextrin mixture was placed in a U-shaped tube. 6 ml of a n-heptane solution of 3 dimethylphenol isomers, i.e., 2,3-dimethylphenol, 3,4-dimethylphenol and 3,5-dimethylphenol, was placed in one vertical tube of the U-shaped tube while 6 ml of n-heptane was placed in the other vertical tube. Vigorous stirring was effected, provided that the bottom portion of the U-shaped tube was partitioned with filter paper. The composition of dimethylphenol isomers extracted in the n-heptane phase after 2 hours is shown in Table 19.

TABLE 19

|  | Raw Material | Oil Extract |
| --- | --- | --- |
| 3,5-Dimethylphenol | 31.4% | 23.2% |
| 2,3-Dimethylphenol | 34.5% | 51.5% |
| 3,4-Dimethylphenol | 34.1% | 25.3% |

Example 20

250 ml of a 10 wt. % aqueous solution of a glucosyl-α-cyclodextrin mixture was placed in a U-shaped tube. 2 ml of a mixture of 3 nitroxylene isomers, i.e., 2-nitro-m-xylene, 4-nitro-m-xylene and 5-nitro-m-xylene, was placed in one vertical tube of the U-shaped tube while 5 ml of n-heptane was placed in the other vertical tube. Vigorous stirring was effected, provided that the bottom portion of the U-shaped tube was partitioned with filter paper. The composition of nitroxylene isomers extracted in the n-heptane phase after 2 hours is shown in Table 20.

TABLE 20

|  | Raw Material | Oil Extract |
| --- | --- | --- |
| 2-Nitro-m-xylene | 34.8% | 72.0% |
| 4-Nitro-m-xylene | 32.5% | 9.5% |
| 5-Nitro-m-xylene | 32.7% | 18.6% |

Example 21

250 ml of a 10 wt. % aqueous solution of a glucosyl-α-cyclodextrin mixture was placed in a U-shaped tube. 0.5 ml of a mixture of 1-methylnaphthalene and 2-methylnaphthalene was placed in one vertical tube of the U-shaped tube while 3 ml of n-heptane was placed in the other vertical tube. Vigorous stirring was effected, provided that the bottom portion of the U-shaped tube was partitioned with filter paper. The composition of methylnaphthalene isomers extracted in the n-heptane phase after 2 hours is shown in Table 21.

TABLE 21

|  | Raw Material | Oil Extract |
| --- | --- | --- |
| 1-Methylnaphthalene | 50.4% | 7.8% |
| 2-Methylnaphthalene | 49.6% | 92.2% |

Example 22

250 ml of a 10 wt. % aqueous solution of a glucosyl-α-cyclodextrin mixture was placed in a U-shaped tube. 0.5 ml of a dimethylnaphthalene mixture (commercially available product) was placed in one vertical tube of the U-shaped tube while 3 ml of n-heptane was placed in the other vertical tube. Vigorous starring was effected, provided that the bottom portion of the U shaped tube was partitioned with filter paper. The composition of dimethylnaphthalene isomers extracted in the n-heptane phase after 90 minutes is shown in Table 22.

TABLE 22

|  | Raw Material | Oil Extract |
| --- | --- | --- |
| 2,6-Dimethylnaphthalene | 10.6% | 42.2% |
| 2,7-Dimethylnaphthalene | 13.5% | 4.0% |
| Other Dimethylnaphthalenes | 75.9% | 53.8% |

Example 23

250 ml of a 10 wt. % aqueous solution of a maltosyl-β-cyclodextrin mixture was placed in a U-shaped tube. 1 ml of a mixture of 2,6-diisopropylnaphthalene and 2,7-diisopropylnaphthalene was placed in one vertical tube of the U-shaped tube while 5 ml of n-heptane was placed in the other vertical tube. Vigorous stirring was effected, provided that the bottom portion of the U-shaped tube was partitioned with filter paper. The composition of diisopropylnaphthalene isomers extracted in the n-heptane phase after 2 hours is shown in Table 23.

TABLE 23

|  | Raw Material | Oil Extract |
| --- | --- | --- |
| 2,6-Diisopropylnaphthalene | 49.2% | 68.2% |
| 2,7-Diisopropylnaphthalene | 50.8% | 31.8% |

Example 24

250 ml of a 10 wt. % aqueous solution of a glucosyl-α-cyclodextrin mixture was placed in a U-shaped tube. 2 ml of a mixture of 2-methylquinoline and 8-methylquinoline was placed in one vertical tube of the U-shaped tube while 10 ml of n-heptane was placed in the other vertical tube. Vigorous stirring was effected, provided that the bottom portion of the U-shaped tube was partitioned with filter paper. The composition of methylquinoline isomers extracted in the n-heptane phase after 1 hour is shown in Table 24.

TABLE 24

|  | Raw Material | Oil Extract |
| --- | --- | --- |
| 2-Methylquinoline | 48.8% | 59.8% |
| 8-Methylquinoline | 51.2% | 40.2% |

Example 25

250 ml of a 10 wt. % aqueous solution of a glucosyl-α-cyclodextrin mixture was placed in a U-shaped tube. 2 ml of a mixture of 7-methylquinoline and 5-methylquinoline was placed in one vertical tube of the U-shaped tube while 10 ml of n-heptane was placed in the other vertical tube. Vigorous stirring was effected, provided that the bottom portion of the U-shaped tube was partitioned with filter paper. The composition of methylquinoline isomers extracted in the n-heptane phase after 1 hour is shown in Table 25.

TABLE 25

|  | Raw Material | Oil Extract |
| --- | --- | --- |
| 7-Methylquinoline | 81.0% | 86.9% |
| 5-Methylquinoline | 19.0% | 13.1% |

Example 26

250 ml of a 20 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 10 ml of n-hexane was placed in the other vertical tube. Vigorous stirring was effected, provided that the bottom portion of the U-shaped tube was partitioned with filter paper. The composition of xylene isomers extracted in the n-hexane phase after 1 hour is shown in Table 26.

TABLE 26

|  | Raw Material | Oil Extract |
|---|---|---|
| p-Xylene | 49.8% | 83.2% |
| m-Xylene | 50.2% | 16.8% |

Example 27

250 ml of a 20 wt. % aqueous solution of a glucosyl-α-cyclodextrin mixture was placed in a U-shaped tube. 30 ml of an about 1:1 mixture of p-xylene and m-xylene was placed in one vertical tube of the U-shaped tube while 40 ml of n-pentane was placed in the other vertical tube. Vigorous stirring was effected, provided that the bottom portion of the U-shaped tube was partitioned with filter paper. After 30 minutes, stirring on the n-pentane phase side was stopped. When the aqueous cyclodextrin phase was separated from the n-pentane phase, about 20 ml of the n-pentane solution of the n-pentane phase was transferred to a distillation apparatus. Thereafter, stirring was continued in the U-shaped tube. On the other hand, extracted xylenes were concentrated with the distillation apparatus, while n-pentane vaporized through distillation was cooled and liquefied, and then returned back to the n-pentane phase in the U-shaped tube. After about 5 minutes, the same procedure as described above was performed. The foregoing procedure was repeated. The composition of xylene isomers concentrated in the distillation apparatus after 6 hours is shown in Table 27.

TABLE 27

|  | Raw Material | Oil Extract |
|---|---|---|
| p-Xylene | 49.8% | 80.8% |
| m-Xylene | 50.2% | 19.2% |

Example 28

100 ml of a 10 wt. % aqueous solution of α-cyclodextrin dissolved in water containing 10 wt. % sodium hydroxide was placed in a U-shaped tube. 20 ml of mixed xylene (commercially available product) was placed in one vertical tube of the U-shaped tube while 20 ml of n-heptane was placed in the other vertical tube. Stirring was effected in such a manner that the xylene phase did not mix with the heptane phase. The composition of xylene isomers extracted in the n-heptane phase after 2 hours is shown in

TABLE 28

|  | Raw Material | Oil Extract |
|---|---|---|
| Ethylbenzene | 15.5% | 20.4% |
| p-Xylene | 18.6% | 23.3% |
| m-Xylene | 43.2% | 42.8% |
| o-Xylene | 22.7% | 13.5% |

Example 29

230 ml of a 10 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 10 ml of n-hexane was placed in the other vertical tube. Vigorous stirring was effected, provided that the bottom portion of the U-shaped tube was partitioned with a rayon nonwoven fabric. The composition of xylene isomers extracted in the n-hexane phase after 1 hour is shown in Table 29.

TABLE 29

|  | Raw Material | Oil Extract |
|---|---|---|
| p-Xylene | 49.9% | 71.0% |
| m-Xylene | 50.1% | 29.0% |

Example 30

230 ml of a 10 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 10 ml of n-hexane was placed in the other vertical tube. Vigorous stirring was effected, provided that the bottom portion of the U-shaped tube was partitioned with a glass fiber filter. The composition of xylene isomers extracted in the n-hexane phase after 1 hour is shown in Table 30.

TABLE 30

|  | Raw Material | Oil Extract |
|---|---|---|
| p-Xylene | 49.9% | 83.4% |
| m-Xylene | 50.1% | 16.6% |

Example 31

230 ml of a 10 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 10 ml of n-heptane was placed in the other vertical tube. Vigorous stirring was effected, provided that the bottom portion of the U-shaped tube was partitioned with a nylon net filter. The composition of xylene isomers extracted in the n-heptane phase after 1 hour is shown in Table 31.

TABLE 31

|  | Raw Material | Oil Extract |
|---|---|---|
| p-Xylene | 50.0% | 82.2% |
| m-Xylene | 50.0% | 17.8% |

Example 32

230 ml of a 10 wt. % aqueous solution of a glucosyl-α-cyclodextrin mixture was placed in a U-shaped tube. 15 ml of an about 1:1 mixture of p-xylene and m-xylene was placed in one vertical tube of the U-shaped tube while 10 ml of n-heptane was placed in the other vertical tube. Vigorous stirring was effected, provided that the bottom portion of the U-shaped tube was partitioned with a filter portion of glass filtration apparatus. The composition of xylene isomers extracted in the n-heptane phase after 1 hour is shown in Table 32.

TABLE 32

|  | Raw Material | Oil Extract |
| --- | --- | --- |
| p-Xylene | 50.0% | 81.2% |
| m-Xylene | 50.0% | 18.8% |

Example 33

230 ml of a 10 wt. % aqueous solution of a glucosyl-α-cyclodextrin mixture was placed in a U-shaped tube. 10 ml of an about 1:1 mixture of p-xylene and m-xylene was placed in one vertical tube of the U-shaped tube while 10 ml of n-heptane was placed in the other vertical tube. Vigorous stirring was effected, provided that the bottom portion of the U-shaped tube was partitioned with a stainless steel net. The composition of xylene extracted in the n-heptane phase after 1 hour is shown in Table 33.

TABLE 33

|  | Raw Material | Oil Extract |
| --- | --- | --- |
| p-Xylene | 50.0% | 77.9% |
| m-Xylene | 50.0% | 22.1% |

Example 34

250 ml of a 10 wt. % aqueous solution of a glucosyl-α-cyclodextrin mixture was placed in a U-shaped tube. 10 ml of an about 1:1 mixture of p-xylene and m-xylene was placed in one vertical tube of the U-shaped tube while 10 ml of n-heptane was placed in the other vertical tube. Vigorous stirring was effected, provided that the bottom portion of the U-shaped tube was partitioned with a silk screen The composition of xylene isomers extracted in the n-heptane phase after 1 hour is shown in Table 34.

TABLE 34

|  | Raw Material | Oil Extract |
| --- | --- | --- |
| p-Xylene | 49.9% | 70.2% |
| m-Xylene | 50.1% | 29.8% |

Example 35

230 ml of a 10 wt. % aqueous solution of a glucosyl-α-cyclodextrin mixture containing 69 g of potassium chloride was placed in a U-shaped tube. 10 ml of an about 1:1 mixture of p-xylene and m-xylene was placed in one vertical tube of the U-shaped tube while 10 ml of n-heptane was placed in the other vertical tube. Vigorous stirring was effected, provided that the bottom portion of the U-shaped tube was partitioned with a nylon net filter. The composition of xylene isomers extracted in the n-heptane phase after 1 hour is shown in Table 35.

TABLE 35

|  | Raw Material | Oil Extract |
| --- | --- | --- |
| p-Xylene | 50.0% | 88.1% |
| m-Xylene | 50.0% | 11.9% |

Example 36

230 ml of a 10 wt. % aqueous solution of a glucosyl-α-cyclodextrin mixture containing 83 g of sodium sulfate was placed in a U-shaped tube. 10 ml of an about 1:1 mixture of p-xylene and m-xylene was placed in one vertical tube of the U-shaped tube while 10 ml of n-heptane was placed in the other vertical tube. Vigorous stirring was effected, provided that the bottom portion of the U-shaped tube was partitioned with a nylon net filter. The composition of xylene isomers extracted in the n-heptane phase after 1 hour is shown in Table 36.

TABLE 36

|  | Raw Material | Oil Extract |
| --- | --- | --- |
| p-Xylene | 50.0% | 87.5% |
| m-Xylene | 50.0% | 12.5% |

Example 37

250 ml of a 10 wt. % aqueous solution of a glucosyl-α-cyclodextrin mixture was placed in a U-shaped tube. 10 ml of an about 1:1 mixture of (1S)-(−)-α-pinene and (1R)-(+)-α-pinene was placed in one vertical tube of the U-shaped tube while 10 ml of n-heptane was placed in the other vertical tube. Vigorous stirring was effected, provided that the bottom portion of the U-shaped tube was partitioned with filter paper. The composition of a-pinene isomers extracted in the n-heptane phase after 90 minutes is shown in Table 37.

TABLE 37

|  | Raw Material | Oil Extract |
| --- | --- | --- |
| (1S)-(−)-α-Pinene | 49.5% | 69.5% |
| (1R)-(+)-α-Pinene | 50.5% | 30.5% |

Example 38

250 ml of a 10 wt. % aqueous solution of a glucosyl-α-cyclodextrin mixture was placed in a U-shaped tube. 10 ml of (±)-limonene was placed in one vertical tube of the U-shaped tube while 10 ml of n-heptane was placed in the other vertical tube. Vigorous stirring was effected, provided that the bottom portion of the U-shaped tube was partitioned with filter paper. The composition of limonene isomers extracted in the n-heptane phase after 90 minutes is shown in Table 38.

TABLE 38

|  | Raw Material | Oil Extract |
|---|---|---|
| (S)-(−)-Limonene | 49.8% | 42.2% |
| (R)-(+)-Limonene | 50.2% | 57.8% |

INDUSTRIAL APPLICABILITY

An operation of selectively inclusion-complexing a compound by an aqueous solution of cyclodextrin and an operation of dissociating and recovering the compound selectively entrapped by the aqueous solution of cyclodextrin from the cyclodextrin have heretofore been performed separately. According to the present invention, these operations can be consecutively performed to make the whole separation process very efficient.

What is claimed is:

1. A continuous and selective inclusion separation method, said method comprising the following steps:
    a) providing a reaction system comprising:
        i) a first organic phase comprising a raw material comprising at least one compound to be separated;
        ii) a second organic phase comprising at least one extraction solvent;
        iii) an aqueous phase comprising at least one inclusion-complexing agent, said aqueous phase simultaneously being in contact with both said first organic phase and said second organic phase so that a first liquid-liquid interface is formed between said first organic phase and said aqueous phase and simultaneously a second liquid-liquid interface is formed between said second organic phase and said aqueous phase; and
        iv) a diaphragm provided in said aqueous phase and distanced from both said first and second liquid-liquid interfaces;
    b) stirring at least a part of the first organic phase and at least a part of the aqueous phase to form oil droplets comprising the raw material in the aqueous phase wherein there is formed at least one inclusion complex comprising a complex of;
        i) said at least one compound; and
        ii) said at least one inclusion-complexing agent;
    c) stirring at least a part of the second organic phase and at least a part of the aqueous phase to form oil droplets comprising said at least one compound separated from said at least one inclusion complex;
wherein said diaphragm is permeable to said complex of said at least one compound and said at least one inclusion-complexing agent, and, upon said stirring, said diaphragm prevents said oil droplets comprising the raw material in the aqueous phase comprising at least one inclusion complex from mixing with said oil droplets comprising said at least one compound separated from said at least one inclusion complex.

2. A continuous and selective inclusion separation method as claimed in 1, wherein said inclusion-complexing agent is at least one cyclodextrin.

3. A continuous and selective inchision separation method as claimed in 1, wherein said raw material containing at least one compound to be separated is a raw material selected from the group consisting of indole-conraining mixtures, disubstituted beuzene isomer mixtures, trisubstituted benzene isomer mixtures, 2-methylquinoline-containing hydrocarbon oils, 7-methylquinoline-containing mixtures, 2,6-diisopropylnaphthalene-containing mixtures, 2-methylnaphthalene-containing mixtures, 2,6-dimethylnaphthalene-containing mixtures, and optical isomer mixtures of pinene. limonene, menthol, and mandelic acid esters.

4. A continuous and selective inclusion separation method as claimed in 1. wherein at least part of a solution as the second organic phase containing a compound extracted thereinto as an object of separation is withdrawn and distilled to concentrate said compound, and the organic solvent separaled by distillation is returned back to the reaction system and reused as the extraction solvent.

* * * * *

UNITED STATES PATENT AND TRADEMARK OFFICE
CERTIFICATE OF CORRECTION

PATENT NO. : 7,030,237 B2
APPLICATION NO. : 10/009627
DATED : April 18, 2006
INVENTOR(S) : Uemasu et al.

It is certified that error appears in the above-identified patent and that said Letters Patent is hereby corrected as shown below:

Column 2, Line 52, "raw a material" should read -- raw material --

Column 2, Line 54, "phase a at compound" should read -- phase a compound --

Column 10, Line 18, "tube 11 The" should read -- tube 11. The --

Column 10, Line 50, "extraction solvent 26" should read -- extraction solvent 25 --

Column 13, Line 50, "260 ml" should read -- 250 ml --

Column 16, Line 16, "maltosyl-62-cyclodextrin" should read
-- maltosyl-β-cyclodextrin --

Column 17, Line 64, "u shaped" should read -- u-shaped --

Column 19, Line 67, "is shown in" should read -- is shown in Table 28. --

Column 22, Line 45, "a-pinene" should read -- α-pinene --

Column 24, Line 21, Claim 2, "inchision" should read -- inclusion --

Column 24, Lines 24-25, Claim 3, "indole-conraining mixtures, disubstituted beuzene" should read -- indole-containing mixtures, disubstituted benzene --

Column 24, Line 31, Claim 3, "pinene. limonene," should read -- pinene, limonene, --

Column 24, Line 34, Claim 4, "1. wherein" should read -- 1, wherein --

UNITED STATES PATENT AND TRADEMARK OFFICE
CERTIFICATE OF CORRECTION

PATENT NO.         : 7,030,237 B2
APPLICATION NO. : 10/009627
DATED              : April 18, 2006
INVENTOR(S)        : Uemasu et al.

It is certified that error appears in the above-identified patent and that said Letters Patent is hereby corrected as shown below:

Column 24, Line 38, Claim 4, "separaled by" should read -- separated by --

Signed and Sealed this

Eleventh Day of September, 2007

JON W. DUDAS
*Director of the United States Patent and Trademark Office*